(12) United States Patent
Bammesberger et al.

(10) Patent No.: US 10,252,273 B2
(45) Date of Patent: Apr. 9, 2019

(54) VALVE FOR DISPENSING A FLUID

(71) Applicant: Roche Diagnostics Operations, Inc., Indianapolis, IN (US)

(72) Inventors: Stefan Borja Bammesberger, Freiburg (DE); Sabrina Kartmann, Freiburg (DE); Peter Koltay, Freiburg (DE); Klaus Mutschler, Freiburg (DE); Juergen Spinke, Lorsch (DE); Laurent Tanguy, Freiburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 112 days.

(21) Appl. No.: 14/530,858

(22) Filed: Nov. 3, 2014

(65) Prior Publication Data
US 2015/0050186 A1 Feb. 19, 2015

Related U.S. Application Data

(63) Continuation of application No. PCT/EP2013/059466, filed on May 7, 2013.

(30) Foreign Application Priority Data

May 8, 2012 (EP) .................................... 12167110

(51) Int. Cl.
*B01L 3/00* (2006.01)
*F16K 99/00* (2006.01)
(Continued)

(52) U.S. Cl.
CPC ............. *B01L 3/567* (2013.01); *B01L 3/0265* (2013.01); *F16K 99/0005* (2013.01);
(Continued)

(58) Field of Classification Search
USPC ........................................................ 422/538
See application file for complete search history.

(56) References Cited

U.S. PATENT DOCUMENTS 3,190,608 A 6/1965 Hassa
3,212,751 A 10/1965 Hassa
(Continued)

FOREIGN PATENT DOCUMENTS

DE 4334350 A1 4/1995
EP 1099483 A1 5/2001
(Continued)

OTHER PUBLICATIONS

International Search Report dated Aug. 1, 2013 in Application No. PCT/EP2013/059466, 3 pages.

*Primary Examiner* — Jill A Warden
*Assistant Examiner* — Brittany I Fisher
(74) *Attorney, Agent, or Firm* — Roche Diagnostics Operations, Inc.

(57) ABSTRACT

A valve for dispensing a fluid comprising a dry portion and a wet portion is presented. Only the wet portion is contacted by the fluid. The wet portion comprises a fluid dispenser unit having a inlet opening, a capillary nozzle providing a fluid outlet, a cavity, the capillary nozzle having an end within the cavity, and a plunger. The plunger moves within the cavity into an opening position allowing an inflow of the fluid through the inlet opening through the cavity and an outflow of the fluid through the capillary nozzle. The plunger has a sealing surface directed towards the end of the capillary nozzle. The plunger moves into a closing position for sealing the end of the capillary nozzle with the sealing surface. The dry portion comprises a closing component for exercising a magnetic closing force onto the plunger for attracting the plunger into the closing position.

16 Claims, 7 Drawing Sheets

(51) Int. Cl.
*G01N 35/00* (2006.01)
*G01N 35/10* (2006.01)
*B01L 3/02* (2006.01)

(52) U.S. Cl.
CPC ..... *F16K 99/0042* (2013.01); *G01N 35/1002* (2013.01); *G01N 35/1016* (2013.01); *B01L 3/52* (2013.01); *B01L 2300/0838* (2013.01); *B01L 2400/0666* (2013.01); *F16K 2099/0084* (2013.01); *G01N 35/0099* (2013.01); *G01N 2035/1034* (2013.01)

(56) References Cited

U.S. PATENT DOCUMENTS

| | | | |
|---|---|---|---|
| 3,738,578 A | 6/1973 | Farrell | |
| 4,458,866 A * | 7/1984 | Graves | F28F 9/005 248/232 |
| 4,489,863 A | 12/1984 | Horchos et al. | |
| 4,852,528 A | 8/1989 | Richeson et al. | |
| 4,899,700 A | 2/1990 | Richeson, Jr. et al. | |
| 5,029,807 A | 7/1991 | Fuchs | |
| 5,741,554 A * | 4/1998 | Tisone | B01L 3/0265 427/424 |
| 5,743,960 A * | 4/1998 | Tisone | B01L 3/0265 118/305 |
| 5,916,524 A * | 6/1999 | Tisone | B01L 3/0265 118/305 |
| 6,050,543 A | 4/2000 | LaGreca et al. | |
| 6,669,909 B2 * | 12/2003 | Shvets | B01L 3/0265 137/487.5 |
| 6,713,021 B1 | 3/2004 | Shvets et al. | |
| 8,109,757 B1 * | 2/2012 | Fusi, III | B29C 33/26 264/328.6 |
| 2002/0088493 A1 * | 7/2002 | Suzuki | G05D 7/0635 137/487.5 |
| 2002/0159919 A1 * | 10/2002 | Churchill | B01J 19/0046 422/400 |
| 2002/0177237 A1 * | 11/2002 | Shvets | B01L 3/0265 436/180 |
| 2005/0224739 A1 * | 10/2005 | Kish, Jr. | F16K 31/0655 251/129.17 |
| 2006/0211132 A1 * | 9/2006 | Miledi | B01J 19/0046 436/180 |
| 2007/0025880 A1 * | 2/2007 | Hoummady | B01L 3/0262 422/400 |
| 2008/0038813 A1 * | 2/2008 | Chen | A61B 5/1427 435/287.2 |
| 2008/0227663 A1 * | 9/2008 | Tisone | B01J 19/0046 506/39 |
| 2010/0051722 A1 * | 3/2010 | Nabih | B05C 5/0225 239/533.1 |
| 2011/0095217 A1 | 4/2011 | Schlenker et al. | |

FOREIGN PATENT DOCUMENTS

| | | |
|---|---|---|
| EP | 1959257 A2 | 8/2008 |
| JP | 2001-235052 A | 8/2001 |
| WO | 1998/004358 A1 | 2/1998 |
| WO | 2009/117995 A1 | 10/2009 |

\* cited by examiner

VALVE FOR DISPENSING A FLUID

CROSS-REFERENCE TO RELATED APPLICATIONS

This application is a continuation of PCT/EP2013/059466, filed May 7, 2013, which is based on and claims priority to EP 12167110.1, filed May 8, 2012, which is hereby incorporated by reference.

BACKGROUND

The present disclosure generally relates to the field of microfluidic dispensing valves and analysis systems for analyzing biological samples.

Today's mechanical pipetting devices used in the microfluidic field, especially in the in-vitro diagnostics, show a limitation in the accuracy and the precision of a dosage of a fluid to be pipetted in the range of 1 µl or less.

Therefore, there is a need for an improved valve, a cartridge and an analyzer system for dispensing a fluid, wherein the dispensing may be performed in the in the sub-microliter range or larger.

SUMMARY

According to the present disclosure, a valve comprising a dry portion and a wet portion, a cartridge and an analyzer system for dispensing a fluid are presented. Only the wet portion is contacted by the fluid. The wet portion comprises a fluid dispenser unit having a fluid inlet opening, a capillary nozzle providing a fluid outlet, a cavity, wherein the capillary nozzle has an end within the cavity, and a plunger. The plunger is movable within the cavity into an opening position by an actuation unit allowing an inflow of the fluid through the fluid inlet opening through the cavity and an outflow of the fluid through the capillary nozzle. The plunger has a sealing surface at its side directed towards the end of the capillary nozzle. The plunger is movable into a closing position closing the end of the capillary nozzle by the sealing surface. The dry portion comprises a closing component for exercising a magnetic closing force onto the plunger for moving the plunger into the closing position. At least one of the closing component and the plunger comprises a permanent magnet for keeping the valve in its normally-closed state.

Accordingly, it is a feature of the embodiments of the present disclosure to provide for an improved valve, a cartridge and an analyzer system for dispensing a fluid, wherein the dispensing may be performed in the in the sub-microliter range or larger. Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A 'normally-closed valve' as understood herein can comprise a valve that can be operated by an actuator, such as by exercising an electromagnetic force. Normally-closed can mean that the valve is in its closed state if the actuator is not energized or if the actuator fails. In other words, unless an opening force is exercised from the actuator onto the valve, the valve can remain in its closed position.

In accordance with some embodiments, the actuation unit may comprise an actuation coil for generating an magnetic field that can exercise a magnetic opening force onto the plunger. For example, actuation can be performed by switching on a power supply of the actuation unit that can cause a current to flow through the actuation coil which, in turn, can build up an electromagnetic field causing the magnetic opening force.

The flow of the electric current through the actuation coil may lead to a temperature increase of the actuation coil. This temperature increase can be limited by the fact that the current may only need to flow in order to bring the valve into its open position and to keep the valve in its open position. No current may need to flow while the valve is in its closed state. This can have the beneficial effect of limiting the temperature increase of the fluid to be dispensed due to the actuation as such a temperature increase may be undesirable depending on the fluid. This can be particularly relevant for fluids that contain living organisms, such as stem cells, which can be sensitive to temperature variations.

In accordance with an embodiment, the plunger and/or the closing component can carry a permanent magnet and/or can comprise of a permanent magnetic material for keeping the valve in its normally-closed state by exercising a magnetic closing force onto the plunger for keeping the plunger in its closing position unless the actuation unit is energized for exercising a counter force onto the plunger that can move the plunger from its closing position into an opening position.

When the actuation unit is switched off, this counter force can disappear such that the plunger can be accelerated towards its closing position and can be abruptly stopped when it reaches its closing position at the end of the capillary nozzle. This impact of the plunger onto the end of the capillary nozzle can have the advantage that a droplet of the dispensed fluid that may be hanging from the tip of the nozzle, i.e. the fluid outlet, can cause the droplet to fall off from the tip of the nozzle so that this droplet may also reach a receptacle into which the fluid is dispensed. This can increase the precision with which the fluid can be dispensed.

It can be a further advantage that the impulse exercised by the plunger when it hits its closing position cannot be exercised on the valve as a whole but directly onto the nozzle such that only a very limited amount of the fluid can be accelerated due to the plunger's impact. This can be particularly advantageous if the fluid is of a highly sensitive nature, such as a fluid containing living organisms, such as stem cells.

A normally-closed valve for dispensing a fluid comprising a dry portion and a wet portion, wherein only the wet portion is arranged to be contacted by the fluid, is presented. The wet portion can comprise a fluid dispenser 121 unit having a fluid inlet opening 120, a capillary nozzle providing a fluid outlet, a cavity, the capillary nozzle having an end within the cavity, and a plunger. The plunger can move within the cavity into an opening position allowing an inflow of the fluid through the fluid inlet opening 120 through the cavity and an outflow of the fluid through the capillary nozzle. The plunger can further have a sealing surface at its side directed towards the end of the capillary nozzle. The plunger can move into a closing position for sealing the end of the capillary nozzle with the sealing surface. The dry portion can comprise a closing component for exercising a magnetic closing force onto the plunger for attracting the plunger into the closing position.

The embodiments may be advantageous, because only the wet portion of the valve may have contact to the fluid, whereas the closing component can be free of any contact with the fluid. As the wet portion and the dry portion are separable, a closing component which can have no contact with the fluid can be reused. On the other hand, the wet portion can be easily disposed after consumption of the respective fluid or reagent. By eliminating the process of washing of the pipette, as it is the case in today's pipetting devices, the carry-over effect and any cross-contamination can be prevented. Producing the wet portion by low-cost materials, the costs per dispensed microliter can be reduced.

When a closing component attracts the plunger in its closing position, the valve can be closed completely so that, for example, a fluid within the valve body of the valve cannot flow out under circumstances such as storage or a transport. According to some embodiments, the closing component can be releasably attached to the wet portion.

The embodiments may be advantageous because the wet portion which can only get in contact with the fluid can be easily separated from the closing component which can be reused for further applications. Whereas the closing component can be reassembled to another wet portion of an unused valve, the wet portion can be easily removed from the dry portion, thus making unnecessary the step of tip washing of the nozzle as it is necessary in nowadays used mechanical pipetting devices. Thus the numbers of steps which may be necessary to prepare the application of another reagent can be reduced. The mechanism for automating the process of dispensing a microfluid can thus be simplified.

According to some embodiments, the closing component can be releasably attached to the wet portion within a direction of the fluid flow through the cavity by a snap fit, a press fit, a form fit, a screw fitting, an adhesive or combinations thereof.

The embodiments may be advantageous because by a further fixing of the wet portion to the closing component in addition to the attractive magnetic force existing between them, the relative position between the two components can be more stabilized thus preventing any leakage in the normally closed state of the valve. Any cross-over effects or any cross-contamination of different fluids in different valves, for example, during a transport or during storage, can be prevented. On the other hand, the dry portion and the wet portion can easily be disassembled in the case of any application. Whereas the disposable wet part, which can be in direct contact with the fluid, can be recycled or disposed, the non-disposable dry part can be reused. So the disposable wet part may be produced by low-cost materials.

According to some embodiments, the fluid dispenser unit can further comprise a plurality of slide faces for guiding the movement of the plunger in the cavity. The slide faces can be interrupted from each other to form a fluid channel through the cavity.

The embodiments may be advantageous because the direction of the movement of the plunger can be guided resulting in a movement parallel to the longitudinal axis of the valve body. When applying a magnetic force to the plunger, there can be no disturbing tilting movements in any uncontrolled directions. Taking into account the adhesive forces of the fluid depending on its degree of viscosity, the amount of the fluid to be dispensed via the nozzle can be reduced in a significant manner thus allowing dispensing droplets of the fluid in the sub-microliter range. So, for example, the amount of a reagent in the field of in-vitro diagnostics can be reduced in a significant manner to perform the desired diagnostic test. The costs of reagents in the field of in-vitro diagnostics can thus be reduced.

According to some embodiments, wherein the slide faces can be arranged at the wall of the cavity extending at least partially between the opening position and the closing position, wherein the slide faces can extend into an axial direction of the cavity, wherein the axial extension of the slide can face towards the fluid outlet can be limited by the closing position, the end of the plunger facing the fluid outlet carrying a sealing surface, the capillary nozzle extending into the cavity such that the capillary nozzle can be operable for balancing the closing force.

The embodiments may be advantageous because the slide faces acting as a duct for the plunger can minimize any tilting of the plunger and reduction of any friction of a parallel movement of the plunger along the long axis of the valve. At the same time any friction during a movement of the plunger can be reduced by the slide faces because of a reduction of the contacted surface during the movement of the plunger. The sealing of the fluid outlet and the additional extension of the capillary nozzle into the cavity can effect that there can be no leakage of the fluid when the plunger is in its closing position. The degree of closing the fluid outlets by the plunger being in its closing position can be increased. At the same time, the degree of accuracy of the dosage can be enhanced by defining a clear closing and opening state of the plunger.

According to some embodiments, the cavity can comprise a sealing region comprising the capillary nozzle. The sealing region can be free of the slide faces.

The embodiments may be advantageous because, if the seal of the plunger expands its volume over a period of time due to an absorption of fluid, a complete sealing of the end of the capillary nozzle can still be possible.

According to some embodiments, the slide faces can be arranged at the outer surface of the plunger and/or the inner surface of the cavity.

The embodiments may be advantageous because the manner of guiding the plunger's movement can be varied according to the characteristics of the magnetic material of the plunger. As the two alternatives of embodiments fulfill the function of guiding the plunger's movement within the cavity in a similar manner, a purchase of the components of the fluid dispenser unit may be focused only on purchase costs.

According to embodiments, the cavity can be formed within a first injection molded part that can have a lower opening. The lower opening can be closed by a second injection molded part with the capillary nozzle extending through the second injection molded part.

The embodiments may be advantageous because the valve body itself could comprise of two parts, with one part connected to a reservoir for a fluid, for example, to a reservoir of a cartridge and another part having an opening for the nozzle and, for example, a protrusion for fitting into an opening of the magnetic closing component. Whereas the first part can be connected to a cartridge reservoir, the second part can be connected with, for example a docking station of an in-vitro diagnostic device. Under the precondition of compatibility, those two parts can be exchanged according to the needs of a diagnostic test. The fact that both parts comprise of an injection molded material, can show that the disposable part of the microfluidic valve can comprise of a low-cost material. The shape and the material of the disposable part can be selected according to the spatial and functional needs of the respective in-vitro diagnostic device. For example, the material may be selected for compatibility with the reagents to be dispensed with this valve or for bio-compatibility.

According to embodiments, the valve can further comprise a holder for receiving the fluid dispenser. The holder can have air ducts at its inner and/or outer surface for thermal isolation of the fluid dispenser.

The embodiments may be advantageous because the air ducts at the inner and/or outer surface of the holder can provide airflow which can affect a thermal isolation of the fluid contained in the valve body of the valve. In the case there is some difference of temperature in the atmosphere surrounding the valve body and the inner space of the valve body, the temperature of the fluid within the valve body can be kept relatively constant with a reduced influence of the temperature of the surrounding atmosphere. The more air ducts at the inner and/or outer surface of the valve body there are, the higher the effect of the thermal isolation can be. In the case there is a device outside of the valve body, for example, an actuation coil, which can produce heat the fluid within the valve body can be protected from being heated in an undesired manner.

According to some embodiment, the holder can have ledges at its inner wall. The ledges can hold the fluid dispenser unit in an operating position.

The embodiments may be advantageous because the ledges at the inner wall of the holder can fix a position of the fluid dispenser by simultaneously reducing the necessary surface to stabilize the position of the fluid dispenser and generating at the same time further air ducts which can contribute to the effect of thermal isolation of the fluid dispenser.

According to some embodiments, the valve can further comprise an actuation unit for exercising a magnetic opening force onto the plunger. The actuation unit can be located outside the wet portion. In one embodiment, the actuation unit can comprise one of an actuation coil or a permanent magnet.

The embodiments may be advantageous because if the actuation unit is located outside the wet portion, the actuation unit itself can have no direct contact with the fluid in the valve body. So the actuation unit can be reused without any change by simply exchanging the wet part of the valve. The actuation unit and the magnet holder can have no contact with the fluid within the valve, the actuation unit and the magnet holder may be releasably attachable to the valve. Thus the flexibility of the valve's application may be increased.

In one embodiment, the actuation unit can be positioned around a holder of the valve with the actuation unit and the holder permanently fixed to a docking station of a device such as, for example, an in-vitro diagnostic device. The actuation unit in the form of an actuation coil or a permanent magnet can generate a magnetic field with the magnetic force causing the plunger within the valve body to move into its opening position or into a position between the opening position and its closing position. The volume of the fluid to be dispensed may be controlled, for example, by defining a time interval in which the nozzle is opened when the plunger is in its opening position and by defining an actuation pressure applied to the fluid which can be responsible for the flow rate mainly.

According to some embodiments, at least one of the closing components and the plunger can be adapted for generating a magnetic field causing the magnetic closing force.

The embodiments may be advantageous because a normally-closed state of the valve can be realized in an efficient way. A complete closing of the valve can be reached so that during storage or a transport a leaking of the reagents and thereby a cross-contamination of different reagents can be prevented. In the normally-closed state of the valve there can be no leakage. A closed state of the valve can be realized by an attractive magnetic force between the closing component and the plunger.

According to some embodiments, at least one of the closing components and the plunger can be a permanent magnet.

The advantage of at least one of the closing components and the plunger being a permanent magnet may be that the valve may be normally closed. In this context, "normally-closed" can mean that the valve can be closed in the case that an electrical current is not supplied to the actuation unit or an electrical current below a actuation threshold is supplied to the actuation unit. The actuation unit can be operable to move the plunger into its opening position by generating a magnetic force when supplied with an electrical current.

The embodiments may be further advantageous, if one of the closing components and the plunger can be, for example, a soft magnet. Hard magnets can have a magnetic coercivity above a predetermined threshold, whereas soft magnets can have a coercivity below a predetermined threshold. As soft magnets are cheaper than hard magnets, costs may be further reduced. In the valve described, the plunger, as a part of the wet portion, may be a soft magnet so that the costs when disposing of the plunger can be low.

A cartridge having a reservoir for receiving a fluid is also presented. The cartridge can comprise a valve according to any of the previous embodiments for dispensing the fluid from the reservoir.

An analysis system for analyzing a biological sample is also presented. The analysis system can comprise a cartridge holder for holding a plurality of cartridges, a sample vessel holder for holding a sample vessel for receiving the biological sample and one or more reagents, a robotic component for a relative movement of the cartridges relative to the sample vessel, a first controller for controlling the robotic component, a second controller for controlling the actuation unit, and a sensor for sensing a quantity of the dispensed fluid.

Figure 1:
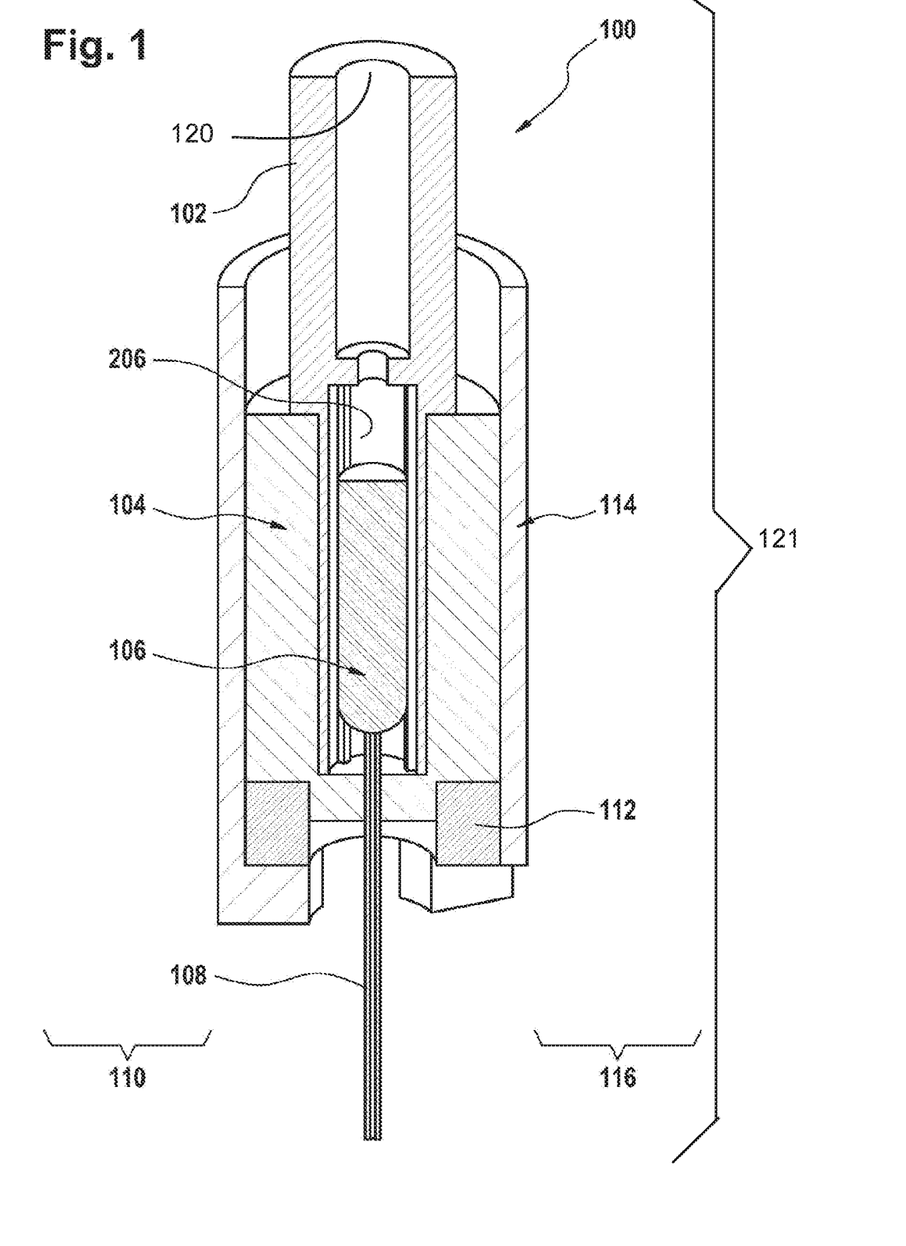
FIG. 1 illustrates a cross-section of the fluid dispenser unit and the closing component inserted into a holder according to an embodiment of the present disclosure.

Referring initially to FIG. 1, FIG. 1 depicts a cross-section of the microfluidic valve 100 positioned in a holder 114, which can comprise a wet portion 110 which can have direct contact with the fluid and can be disposable, and a dry portion comprising a closing component 112. The holder 114 and the closing component 112 may not come into contact with the fluid and may be reused for another application. So the latter elements may be treated as non-disposable components 116.

The disposable part 110 can comprise a first valve body 102 plugged into a second part 104 of the valve body, a plunger 106 movable in a cavity 206 formed by the first part 102 of the valve body as well as a capillary nozzle 108 extending into the cavity 206 of the first part 102 of the valve body. The disposable part 110 of the microfluidic valve 100 can be characterized by the fact that the components of the wet portion, comprising the first valve body 102, the second valve body 104, the plunger 106 and the capillary nozzle 108, can have direct contact with a fluid to be dispensed by the microfluidic valve.

The non-disposable components 116 comprising the closing component 112 and the holder 114 may not have direct contact with the fluid to be dispensed by the microfluidic valve.

Figure 2:
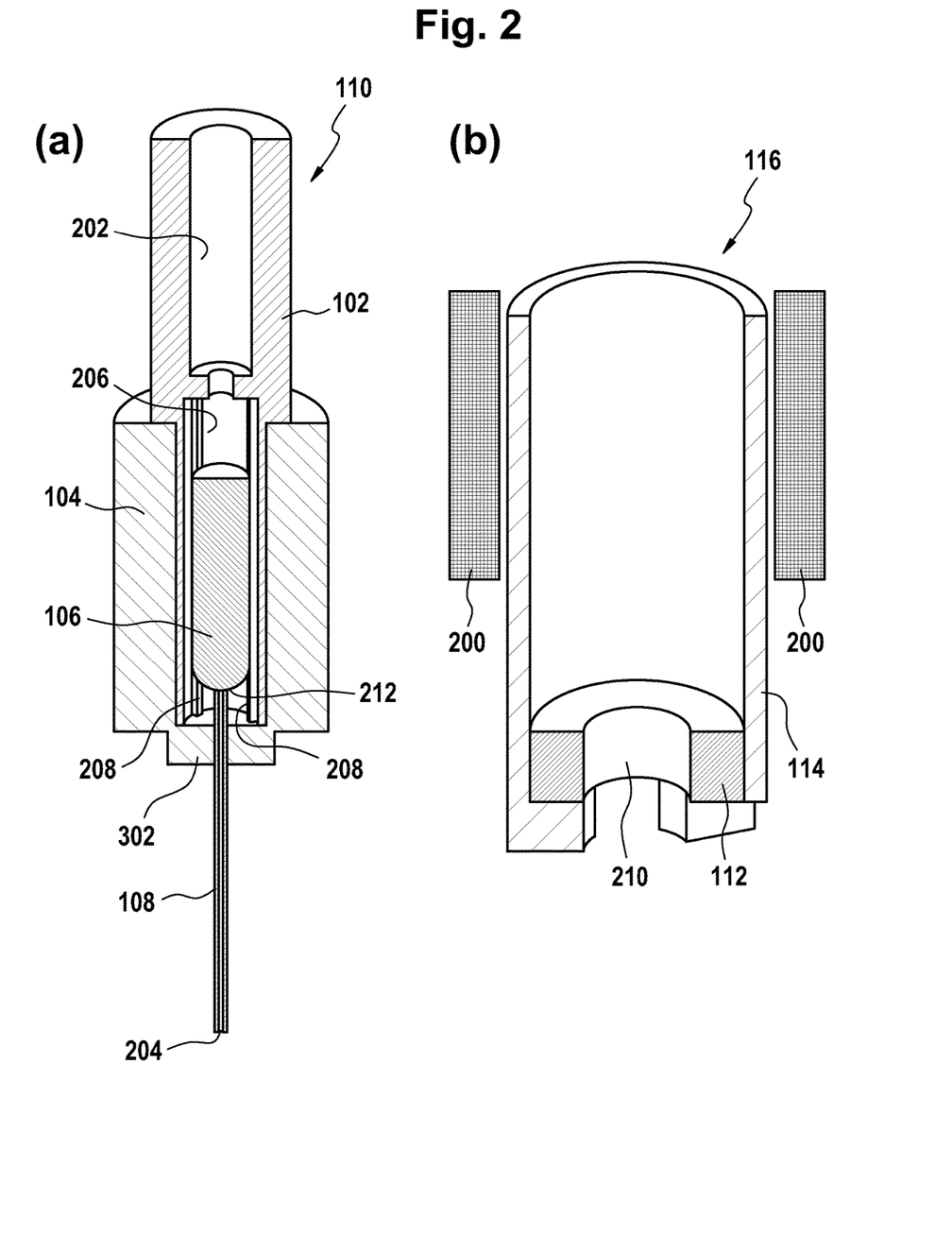
FIG. 2 illustrates the disposable wet portion (a) and the non-disposable part surrounded by an actuation unit according to an embodiment of the present disclosure.
Figure 6:
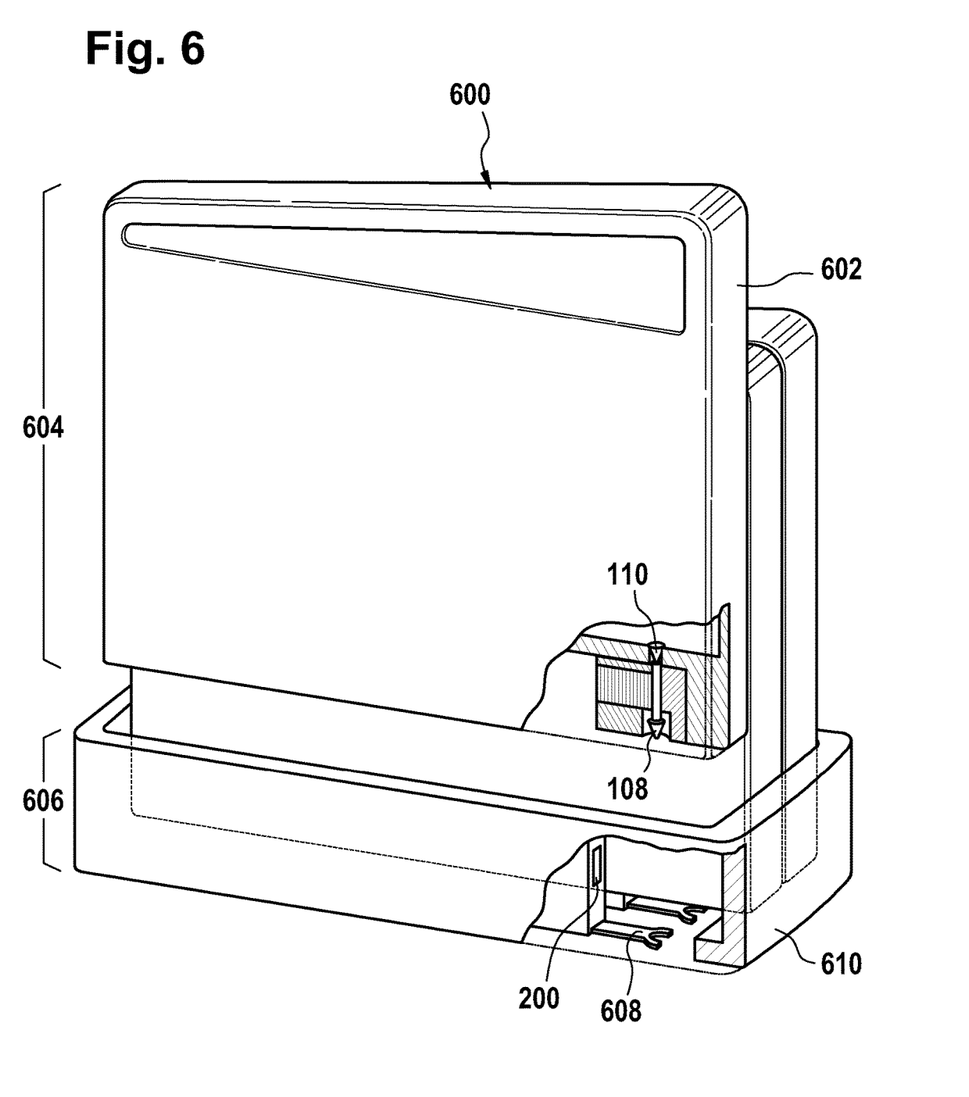
FIG. 6 illustrates a cartridge according to an embodiment of the present disclosure.

FIG. 2a depicts the wet portion 110 of the microfluidic valve 100. Together with the closing component, for example, with the closing component 112 as shown in FIG. 2b, the wet portion can form the microfluidic valve. The first part 102 of the valve body can have a connection 202 to a reservoir such as, for example, a cartridge 600 as shown in FIG. 6, containing a reagent. Between this connection 202 and the end of the capillary nozzle 108 extending into the cavity 206 of the first part of the valve body 102, there can be a duct for the plunger 106 with slide faces 208 at the inner wall of the cavity 206. The plunger 106, which can be coated with a bio-compatible substance, can be upwards and downwards movable in the cavity 206. The slide faces 208 can guide the movement of the plunger 106 and prevent the plunger 106 from any tilting. The plunger 106 may have a sealing surface 212 on the end which is in contact with the capillary nozzle 108. The sealing surface 212 can enable the plunger 106 to completely close a fluid outlet 204 of the capillary nozzle 108.

The second part 104 of the valve body can have a protrusion 302 so that the valve body can be easily plugged into an opening 210 of the closing component 112. The closing component 112 can form the dry portion of the microfluidic valve because it has no direct contact with the fluid, which for a dispensing by the valve is to be found in the cavity 206 after having passed the connection 202 to the fluid reservoir of, for example, a cartridge reservoir containing the fluid. So the closing component 112 can form the dry portion of the microfluidic valve, which can be reused and can be treated as non-disposable. The holder 114 and an external actuation unit 200 can form other non-disposable components which therefore can be fixed permanently to, for example, a docking station of an analyzer serving for the automated execution of tests in the field of in-vitro diagnostics.

The plunger 106 and the closing component 112 may be made of materials having ferromagnetic properties, whereby at least one of the two may be a permanent magnet. Thus they may attract each other so that the plunger 106 can be in its closing position in the normal state of the valve, thereby closing the fluid outlet of the capillary nozzle 108. Thus in a normal state of the microfluidic valve, the valve can be closed preventing the fluid to leave the cavity 206 via the capillary nozzle 108. That the valve can be closed in its normal state can be advantageous in the case the valve containing a fluid is transported or stored.

The actuation unit 200 can be able to generate a magnetic field which can be able to over-compensate the attractive magnetic force between the plunger 106 and the closing component 112. In this case, the plunger 106 can move away from the direction of the closing component 112 so that the fluid outlet of the capillary nozzle 108 can be opened and any fluid contained in the cavity 206 can leave the valve body via the fluid outlet of the capillary nozzle 108. When the plunger 106 is moved upwards, the fluid can flow through the space between the slide faces 208 downwards into the direction of the capillary nozzle 108. A fluidic resistance of the valve can determine a flow rate of the fluid when being dispensed by the valve.

Figure 3:
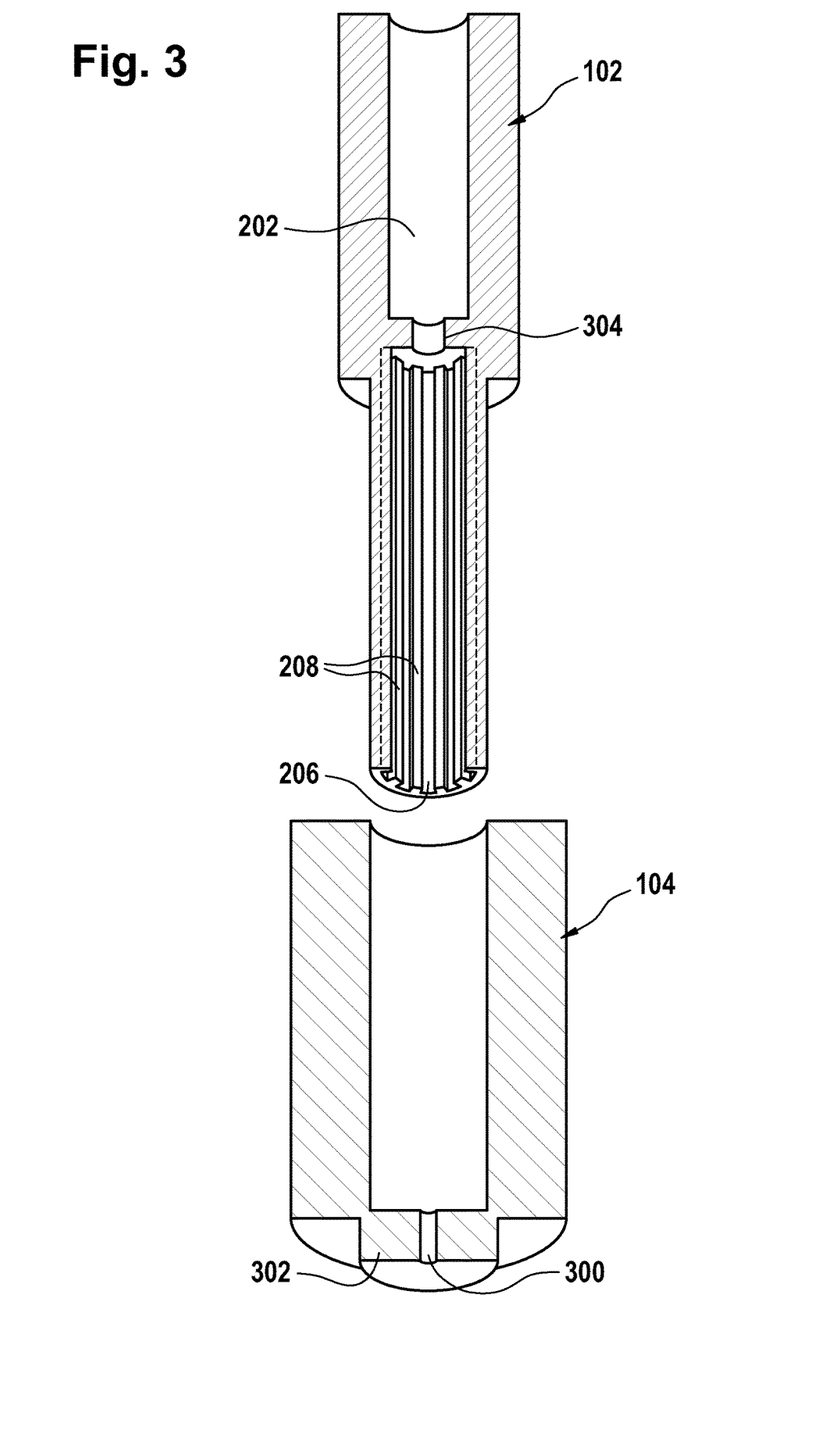
FIG. 3 illustrates the two injection molded parts of the valve body according to an embodiment of the present disclosure.

FIG. 3 depicts a cross-section of the first part 102 and the second part 104 of the valve body with the first part and the second part separated from each other. The first part 104 of the valve body can have a spatial narrowing 304 between the connection 202 to a fluid reservoir and the cavity 206. By the spatial narrowing 304 of the diameter, the stroke length of the movement of the plunger 106 can be limited in the direction of the connection 202 of the fluid reservoir. The first part 104 can also have slide faces 208 for guiding the movement of the plunger 106.

The second part 104 of the valve body can have a protrusion 302 for fitting into the opening 210 of the closing component 112. Via the opening 300 for the capillary nozzle 108, the fluid within the valve body can leave the second part 104 of the valve body via the capillary nozzle 108 during the dispensing process.

The first part 102 and the second part 104 of the valve body can be injection molded parts so that the shapes of the two parts can be adapted to each other. As shown in FIG. 3, the shape of the first part 102 of the valve body can be adequate for an insertion of the first part 102 of the valve body into the second part 104 of the valve body so that a relative position between the two parts of the valve body can be even attained by a simple plug-in process. The connection between the first and the second part of the valve body can be supported by other means, for example, by an adhesive.

Figure 4:
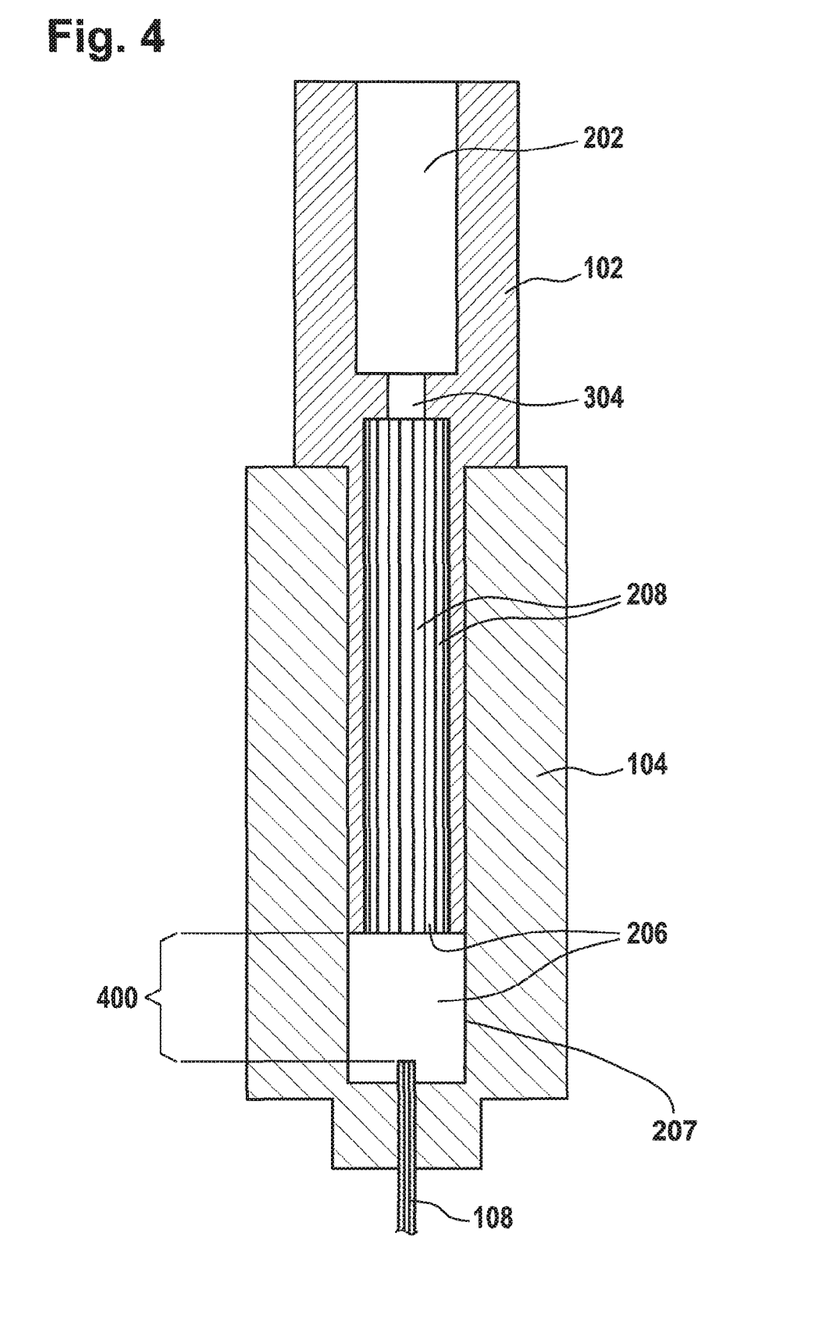
FIG. 4 illustrates a cross-section of the dispensing valve according to an embodiment of the present disclosure.

FIG. 4 depicts a cross-section of the valve body of the microfluidic valve. As can be seen in FIG. 4, in the area of the valve seat 400 of the second part 104 of the valve body, the cavity 206 for the plunger 106, or the sealing region 207 comprised in the cavity 206, can be free of slide faces 208. Thus the fluid outlet via the capillary nozzle 108 can be totally closed because there can be a prevention of any friction force caused by the expansion of the sealing layer or surface preventing the plunger 106 from moving into its closing position. The plunger 106 can comprise of a hygroscopic material with increasing volume and therefore also increasing diameter because of soaking a little part of the fluid in the course of time, the absence of the slide faces can allow the plunger to move into its closing position even if its diameter has increased. So any leakage can be prevented.

Figure 5:
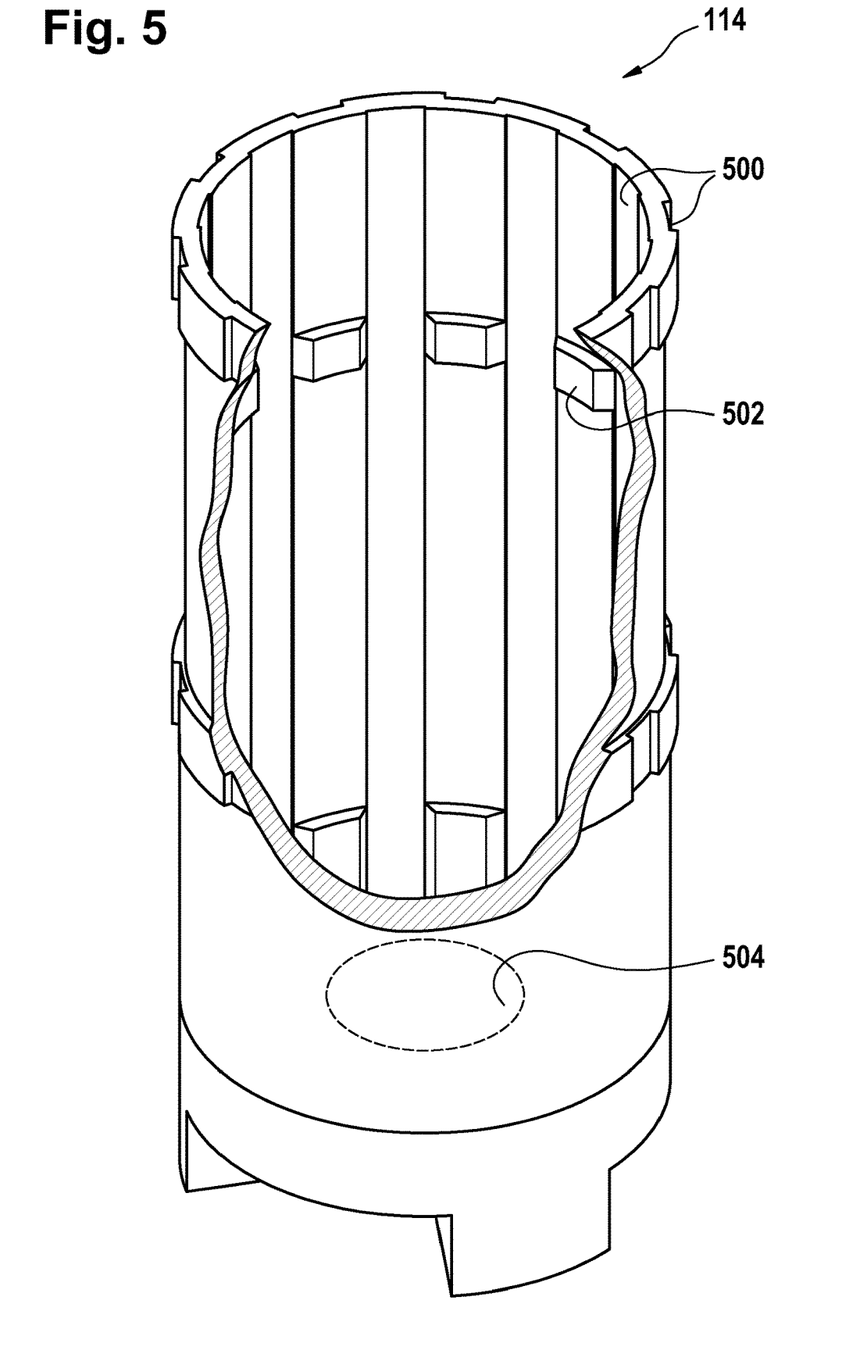
FIG. 5 illustrates a holder showing air ducts and ledges according to an embodiment of the present disclosure.

FIG. 5 depicts a holder 114 for stabilizing a relative position between the valve body (102 and 104), the closing component 112 and the actuation unit 200. The second part 104 of the valve body can be positioned in the hollow cylinder with parts of its boundaries formed by the ledges 502. The closing component 112 can be positioned at the bottom of the holder 114. The actuation unit 200 can be positioned around the holder 114. The holder 114 can stabilize the relative position of the components of the electromagnetic microfluidic valve 100 and its actuation unit 200. So the effect of the magnetic fields cannot be distorted by any uncontrolled relative movements between the components of the microfluidic valve 100 and its actuation unit 200. At the bottom of the holder 114, there can be an opening 504 for allowing an extension of the capillary nozzle 108.

The holder 114 can have air ducts 500 at its inner and outer surface. Further, air ducts can be generated when the second part 104 of the valve body is positioned between the ledges 502. The air ducts 500 can affect a thermal isolation by increasing the number of boundary layers. The actuation unit 200 can be an actuation coil which can produce some heat during its actuation, the air ducts 500 of the holder 114 can prevent the fluid in the cavity 206 of the second part 104 of the valve body from being heated, too.

FIG. 6 depicts a cartridge where the microfluidic dispenser unit 110 has been integrated. The reservoir 602 for a reagent, the wet portion of the microfluidic dispenser unit 110 and its capillary nozzle 108 can form the disposable part 604 of a cartridge system. A cartridge system may comprise several fluid reservoirs and wet portions of dispenser units 110 which can be permanently fixed to each other. Each fluid reservoir can contain another reagent, so that for a changing of the reagent for a diagnostic test, the cartridge system may only need to be moved from one position to another. An automatism for executing a series of diagnostic tests for one sample may be facilitated.

The fluid reservoirs may be closed at least during transport and storage so that a fluid contained in fluid reservoir can be encapsulated from an outer environment. Any volatilization and any contamination of the reagent may thus be prevented. The on-board stability of reagents used for diagnostic tests may be increased. In some embodiments, there may be a vent that can be opened after transport or storage to allow the equalization of pressure in the fluid reservoir.

The non-disposable part 606 of the cartridge system can comprise the actuation unit 200 and a sensor 608 as well as the cartridge holder 610. Whereas the actuation unit 200 can activate the dispensing process by the dispensing unit via the capillary nozzle 108, the sensor 608 can sense a quantity of the dispensed fluid and/or can perform a quality checks, if fluid has been dispensed or not. The non-disposable part of the cartridge system can be permanently fixed to a docking station of a device serving, for example, for an automated execution of in-vitro diagnostic tests by a robotic component.

Figure 7:
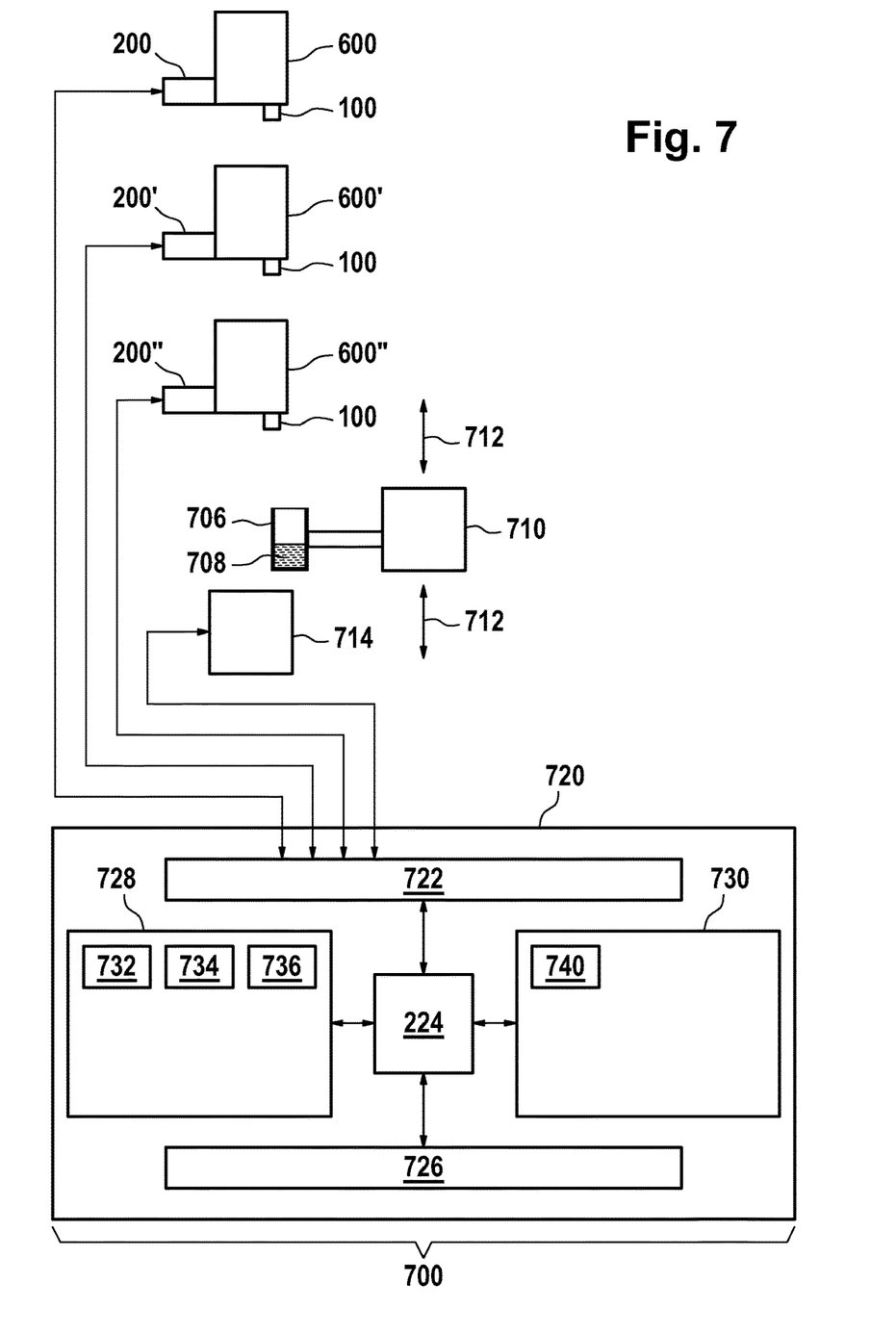
FIG. 7 illustrates an automatic analyzer according to an embodiment of the present disclosure.

FIG. 7 illustrates an automatic analyzer 700. This automatic analyzer is shown as having three cartridges 600, 600' and 600". There can be an actuation unit 200 connected to cartridge 600. There can be an actuation unit 200' attached to cartridge 600'. There can be an actuation unit 200" attached to cartridge 600". The actuation units 200, 200', 200" can be for actuating the dispenser 100 of the cartridges 600, 600' and 600". The automatic analyzer 700 is shown as having a relative mover 710 which can provide relative movement 712 between a sample holder 706 and the cartridges 600, 600' and 600'". The sample holder 706 is shown as containing a biological sample 708. The cartridges 600, 600', 600" may be used to add one or more fluids to the biological sample 708. The automatic analyzer 700 is shown as further containing a detection system 714, which is optional. The detection system 714 may optionally comprises one or more sensors for measuring a physical quantity or physical property of the biological sample 708. For example, the detection system 714 may comprise an NMR system, an optical transmission or reflectance measurement system, an electrochemical or optical sensor, a pH meter, a camera system, capacitive sensors and/or a chromatography system. The relative mover 710 can also be operable for moving the sample holder 706 to the detection system 714.

The arrangement of the cartridges 600, 600' and 600" and the detection system 714 can be representative. In some embodiments, the sample holder 706 may remain in a fixed position and the cartridges 600, 600' and 600" may move. The actuation systems 200, 200', 200" and the detection system 714 are shown as being connected to a hardware interface 722 of a computer system 720. The computer system 770 can function as a controller for the automatic analyzer 700. The computer 720 is further shown as containing a processor 774 which can be able to control the operation and function of the automatic analyzer 700 using the hardware interface 722. The processor 724 is shown as further being connected to a user interface 726, computer storage 728 and computer memory 730. The computer storage 728 is shown as containing an analysis request 732. The analysis request 732 can contain a request to analyze the biological sample 708.

The computer storage 728 is shown as further containing sensor data 734 received from the detection system 714. The computer storage 728 is shown as further containing an analysis result 736 which can be determined using the sensor data 734. The computer memory 730 can contain a control module 740. The control module 740 can contain computer executable code which can enable the processor 724 to control the operation and function of the automatic analyzer 700. For instance, the control module 740 may use the analysis request 732 to generate commands to generate and send to the actuation systems 200, 200', 200", the detection system 714 and the relative movement system 710. The control module 740 may also generate the analysis result 736 using the sensor data 734.

The described microfluidic valve may make washing the wet portion after dispensing fluid unnecessary. The wet portion can be easily disposed after the reagent is consumed. In other words, after the fluid stored in the wet portion and the connected fluid reservoir is consumed the entire wet portion may be replaced.

The wet portion may be produced from low-cost materials. The usage of an unused wet part for the next application of another reagent can prevent a carry-over of the respective reagent having been used before and consequently a cross-contamination.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

We claim:

1. A valve for dispensing a fluid comprising a dry portion and a wet portion, wherein only the wet portion is contacted by the fluid, the wet portion comprising:
   a fluid dispenser unit having a fluid inlet opening,
   a capillary nozzle providing a fluid outlet,
   a cavity, wherein the capillary nozzle has an end within the cavity, and
   a plunger, wherein the plunger is movable within the cavity into an opening position by an actuation unit allowing an inflow of the fluid through the fluid inlet opening through the cavity and an outflow of the fluid through the capillary nozzle, wherein the plunger has a sealing surface at its side directed towards the end of the capillary nozzle, and wherein the plunger is movable into a closing position closing the end of the capillary nozzle by the sealing surface; and
   the dry portion comprising:
   a closing component for exercising a magnetic closing force onto the plunger for moving the plunger into the closing position, wherein at least one of the closing component and the plunger comprises a permanent magnet and the other comprises a ferromagnetic material, wherein the magnetic closing force is generated by the ferromagnetic material and the permanent magnet for keeping the valve in its normally-closed state,
   wherein the end of the capillary nozzle is located between the closing component and the sealing surface, both in the normally-closed and in an open state of the valve.

2. The valve according to claim 1, wherein the closing component is releasably attached to the wet portion.

3. The valve according to claim 2, wherein the closing component is releasably attached to the wet portion within a direction of the fluid flow through the cavity by a snap fit, a press fit, a form fit, a screw fitting, an adhesive or combinations thereof.

4. The valve according to claim 1, wherein the fluid dispenser unit further comprises a plurality of slide faces for guiding the movement of the plunger in the cavity, wherein the slide faces are interrupted for forming a fluid channel through the cavity.

5. The valve according to claim 4, wherein the slide faces are arranged on a wall of the cavity extending at least partially between the opening position and the closing position, wherein the slide faces extend in an axial direction of the cavity, wherein the axial extension of the slide faces towards the fluid outlet is limited by the closing position, wherein the end of the plunger facing the fluid outlet comprises a sealing surface, and wherein the capillary nozzle extends into the cavity such that the capillary nozzle is operable for balancing the closing force.

6. The valve according to claim 5, wherein the cavity has a sealing region surrounding the capillary nozzle and wherein the sealing region is free of the slide faces.

7. The valve according to claim 4, wherein the slide faces are arranged at the outer surface of the plunger or the inner surface of the cavity.

8. The valve according to claim 1, wherein the cavity is formed within a first injection molded part that has a lower opening, wherein the lower opening is closed by a second injection molded part and wherein the capillary nozzle extends through the second injection molded part.

9. The valve according to claim 1, further comprises,
   a holder for receiving the fluid dispenser, wherein the holder has air ducts at its inner and/or outer surface for thermal isolation of the fluid dispenser.

10. The valve according to claim 9, wherein the holder has ledges at an inner wall, wherein the ledges are configured to hold the fluid dispenser unit in an operating position.

11. The valve according to claim 1, wherein the actuation unit for exercising a magnetic opening forces onto the plunger is located outside the wet portion.

12. The valve according to claim 1, wherein the actuation unit comprises one of an actuation coil or a permanent magnet.

13. The valve according to claim 1, wherein the sealing surface is formed by a sealing layer.

14. The valve according to claim 1, wherein the closing component comprises the permanent magnet and wherein the plunger comprises a soft magnet.

15. A cartridge having a reservoir for receiving a fluid, wherein the cartridge comprises a valve according to claim 1 for dispensing the fluid from the reservoir.

16. An analysis system for analyzing a biological sample, the analysis system comprising:
    a cartridge holder for holding a plurality of cartridges according to claim 15;
    a sample vessel holder for holding a sample vessel for receiving the biological sample and one or more reagents;
    a robotic component configured to provide relative movement of the cartridges in the cartridge holder relative to the sample vessel;
    a sensor for sensing a quantity of the dispensed fluid and for generating commands based on the quality of the dispensed fluid;
    a first controller for controlling the relative movement of the robotic component between the cartridges and the sample vessel based on commands received from the sensor; and
    a second controller for controlling the actuation unit based on commands received from the sensor.

* * * * *